(12) United States Patent
Vassarotti

(10) Patent No.: US 6,372,144 B1
(45) Date of Patent: Apr. 16, 2002

(54) METHOD FOR CONCENTRATING OR WASHING MACROMOLECULES IN A SOLUTION AND DEVICE FOR CARRYING OUT SAID METHOD

(75) Inventor: Vincenzo Vassarotti, Bugnaux sur Rolle (CH)

(73) Assignee: Vivascience AG, Hannover (DE)

( * ) Notice: Subject to any disclaimer, the term of this patent is extended or adjusted under 35 U.S.C. 154(b) by 0 days.

(21) Appl. No.: 08/472,965

(22) Filed: Jun. 7, 1995

(30) Foreign Application Priority Data

Jun. 13, 1994 (SE) ............................................. 9402076

(51) Int. Cl.[7] ............................................. B01D 61/00
(52) U.S. Cl. .................. 210/650; 210/651; 210/327.84; 210/346; 210/261; 210/653; 422/101
(58) Field of Search ........................... 210/321.84, 346, 210/261, 650, 651, 653, 505, 445; 436/807, 163; 422/101

(56) References Cited

U.S. PATENT DOCUMENTS 2,879,207 A * 3/1959 Poitras .................. 210/321.84
3,817,379 A * 6/1974 Zipilivan et al. ........... 210/346
4,162,979 A * 7/1979 Wahlefeld et al. .......... 210/282
4,208,187 A * 6/1980 Givner ....................... 210/645
4,623,461 A * 11/1986 Hossom et al. ............. 210/445
5,092,997 A * 3/1992 Siegert .................. 210/321.84

* cited by examiner

Primary Examiner—Ana Fortuna
(74) Attorney, Agent, or Firm—Young & Thompson

(57) ABSTRACT

A device for removing or replacing solvent in a liquid sample containing macromolecules includes a concentration chamber having an aperture adjacent to the upper end of the concentration chamber which is arranged to receive and tightly fix the outlet of a detachable auxiliary reservoir. In methods employing the device, the concentration chamber is filled with part of a liquid sample to a predetermined level, and a detachable auxiliary upper reservoir containing the rest of the liquid sample is tightly fixed to the aperture adjacent to the upper end of the concentration chamber to successively deliver additional liquid sample as the concentration is progressing, or a detachable auxiliary upper reservoir containing a solvent or buffer solution is tightly fixed to the aperture adjacent to the upper end of the concentration chamber to successively deliver solvent or buffer solution as a replacement for the liquid absorbed by an absorption material.

16 Claims, 2 Drawing Sheets

METHOD FOR CONCENTRATING OR WASHING MACROMOLECULES IN A SOLUTION AND DEVICE FOR CARRYING OUT SAID METHOD

TECHNICAL FIELD

The present invention relates to a method for removing solvent or game generally liquid from a liquid sample containing macromolecules or for washing said molecules i.e. replacing the solvent and a device for carrying out this method.

BACKGROUND ART

There has been a number of analytical procedures developed in the biochemical art wherein it is required to remove solvent from e.g. protein solutions in order to have a more concentrated protein sample which can be analyzed effectively, or to remove low molecular weight ions or solutes. Many other analytical procedures involving not only proteins but macromolecular species in general, have also been developed wherein it is necessary to concentrate a macromolecular component in a liquid sample.

When concentrating small volumes of macromolecules in solution using an absorbent media which draws solute through a filter in the form of a thin membrane by capillary action there exists the problem of achieving a sufficiently fast filtration which is in contrast with the need to reduce the effective membrane area in order to minimize loss of macromolecular material which tends to bind to the filter structure during filtration.

In known devices, of the type referred to here, the contact between the absorbent and the membrane will limit the possible storage time of the device. The membrane structure is provided with wetting agents required to maintain the prameters for, the fluid transport through the membrane. During storage the absorbent will absorb these wetting agents and thus deteriorate the membrane.

The US: patent, U.S. Pat. No. 3,817,379 describes a disposable device for concentrating liquid specimens by filtration or ultrafiltration having a chamber with one wall formed of a membrane permeable to the liquid vehicle of the specimen and a layer of solid absorbent material pressed against the membrane outside of the chamber.

In this device the large effective filter area available at the start of the concentration is rapidly reduced as the concentration proceeds. The concentration speed will thus decrease. The use of a large initial filtration area also increases absorption losses on the membrane surface as mentioned above. This limits the volume range for the samples which can be used with this device and requires that alternative sizes of devices be offered.

If a larger volume than could initially be filled into the device is to be concentrated the device could of course be refilled. This would, however, mean that someone had to attend to the refilling which is not very convenient. Especially when several samples of liquid are concentrated simultaneously in parallel, possibly in a multiple concentrator device as shown in U.S. Pat. No. 3,817,379 having several compartments, refilling considerably increases the risk of cross contamination by mistake.

In a device of this type with one single membrane for several cells there is also the possibility of osmotic effect between adjacent: cells which would contaminate the retentates. Interaction between adjacent cells could of course also be due to poor sealing between the cells.

Due to the irregularities in the absorbent surface and the difficulty in obtaining a perfectly flat membrane surface, not all parts of the membrane are in contact with the absorbent material even if a resilient spongy material that compresses the absorbent sheet against the back of the membrane material should be used. The resultant reduction of absorptive surface area in contact with the membrane reduces the speed of filtration and the random contact points against the membrane surface further results in significant differences in concentration time between devices.

Another disadvantage with this device is that the relatively low hydrostatic pressure in the solute against the membrane surface will result in an extended period of time for the membrane and its support to be wetted out so that the capillary filtration can begin.

A further disadvantage is the capillary dimension of the filling and concentrate removal channel which requires the use of a specific glass Pasteur pipette which makes sample filling laborious and does not allow a precise quantitative recovery of final concentrate volume. The final concentrate must be first removed to a separate container before being again transferred for analysis by a conical quantitative pipette.

SUMMARY OF THE INVENTION

The problems of the prior art are overcome by the provision of a method and a device for carrying out said method as defined in the appended claims.

An advantageous embodiment of the invention will provide variability in effective membrane area so as to achieve the best relationship between concentration speed and protein absorption on the membrane surface.

The same embodiment will make it possible to separate the absorbent material from the membrane structure during transport and storage in order di to avoid drying out of the membrane wetting agents by the absorbent material.

It is an object of the invention to provide a concentrating device having a low volume filtration or concentration chamber preferably in the form of a flat, thin compartment, in the side wall of the membrane is mounted, arranged below a detachable sample reservoir which seals onto the concentration chamber by means of a conical or any other type of seal arrangement.

Whilst allowing increased flexibility for different sample volumes by changing the volume of the detachable reservoir without a change in membrane area this arrangement maximizes sample contact time with the total membrane surface during an extended period of the concentration. In the device according to the US patent above, the sample contact time with the total membrane surface is limit ed to the very first instant of the concentration procedure.

It is another object of the invention to provide improved hydrostatic pressure on the membrane surface to speed up the time required to wet out the membrane surface and supporting material and to assist the capillary action of the absorbent material during the initial stages of concentration.

It is another object of t invention to provide a filling aperture that supports the conical tip of a standard 10 ml pipette to provide easier filling in a single step.

It is another object of the invention to provide a concentrate recovery method that utilizes standard conical micro volume pipette tips to allow direct quantitative transfer of the concentrated sample without the need for an intermediate vessel.

It is another object of this invention to provide a concentrator which gives constant final volume in a separate concentrate pocket arranged below and efficiently separated from the active surface area of the membrane.

It is another object of the invention to maximize membrane yield to reduce manufacturing cost. The efficiency of the device will make it possible to use a much smaller membrane area for the same or shorter total concentration time as in a device according to the prior art.

It is another object of the invention to provide a multiple device in which the risk of cross contamination between adjacent cells is eliminated.

Further advantages and characteristics of the invention will be apparent from the following description.

BRIEF DESCRIPTION OF THE DRAWINGS

The following description of the invention will be made with reference to the accompanying drawings on which FIGS. 1 a–c show three different views of a device according to the invention.

DETAILED DESCRIPTION OF THE INVENTION

Figure 1A:
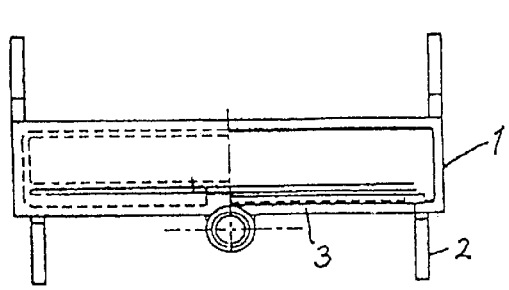

FIGS. 1 a–c show three different views of an embodiment according to the invention. The main parts of the device are an absorbent container 1 in the form of a parallelepiped provided with feet 2 which keep the device steady standing on a support surface during the concentration procedure, a concentration chamber 3 mounted in an aperture 4 in the sidewall of said container and a detachable upper reservoir 5 on top of the concentration chamber 3.

The absorbent container 1 could be provided with a lid 6 to minimize the evaporation from the container during the process, and in the case when the absorbent material is in the form of a powder or gel, keep this in place during shipping and storage. The concentration chamber 3 could of course be an integrated part of the absorbent container, but the arrangement with separate units according to FIGS. 1 a–c will give lower manufacturing costs and has certain other advantages, cf. below. As will be described below the detachable upper reservoir 5 could preferably be a standard laboratory pipette which is being used to fill the concentration chamber with the liquid to be processed and is then being fixed liquid-tight to the top of the chamber and will then constitute a supplementary reservoir of liquid. The liquid column in the pipette will raise the hydrostatic pressure in the concentration chamber which will speed up the concentration process.

The concentration chamber 3, according to the shown embodiment, has a generally flat, rectangular form with one diagonal arranged vertically. It should, however, be noted that other geometrical forms could be used for the concentration chamber, e.g. a generally triangular form. One of the large flat surfaces is constituted by a membrane 7 which could be a normal ultrafiltration or microporous membrane as in similar devices. The chamber could also be provided on the inside with vertical membrane support ribs (not shown). The membrane side of the chamber is turned towards the absorbent material in the container 1. The opposite side-wall is provided with a pipette receiving portion 8 as shown in e.g. FIG. 2. The general form of this portion is conical which means that the chamber on one hand can be provided with an opening large enough for a standard laboratory pipette and on the other hand that the volume of the chamber is increasing upwards with the effect that the decrease in effective membrane area during the final part of the concentration process is retarded.

The arrangement with a detachable upper reservoir 5 will considerably decrease the concentration time. It should be noted that the effective membrane surface will be constant during the main part of the process. A typical volume of the concentration chamber could be 2,5 ml which means that the concentration will take place with constant, maximum effective membrane area until the remaining volume has reached 2,5 ml. From this point on the area of the effective membrane will decrease. As mentioned above, however, the decrease could be retarded due to a design of the chamber giving said chamber an appropriate remaining volume as a function of the liquid level in said chamber.

Comparing tests have been carried out using a device according to U.S. Pat. No. 3,817,379 and a device according to the invention. With a starting volume of the test liquid of 10 ml the prior art device will be completely filled up and the liquid will be in contact with the full membrane area of 28 $cm^2$ at the start of the process.

In the device according to the invention somewhat more than 2 ml would fill up the concentration chamber having a membrane of the same type with a surface of 16 $cm^2$ (the tip of the pipette would take away some volume from the nominal 2,5 ml) and the rest, i.e about 8 ml would still remain in the upper reservoir 5 at the start of the process.

To reach a 100×concentration would take around 180 min in the device according to the prior art and 120 min in the device according to the invention. Thus, the new device is in this test 30% faster than the traditional one and this result is achieved with a membrane area which is 43% smaller.

The advantages are apparent especially when taking into consideration the fact that the membrane is a very expensive part of the device. As the membrane area is smaller you also get the additional effect of less loss of macromolecular material bound to the membrane surface during the concentration process. This means that the quality of the retentate will be higher.

Figure 1B:
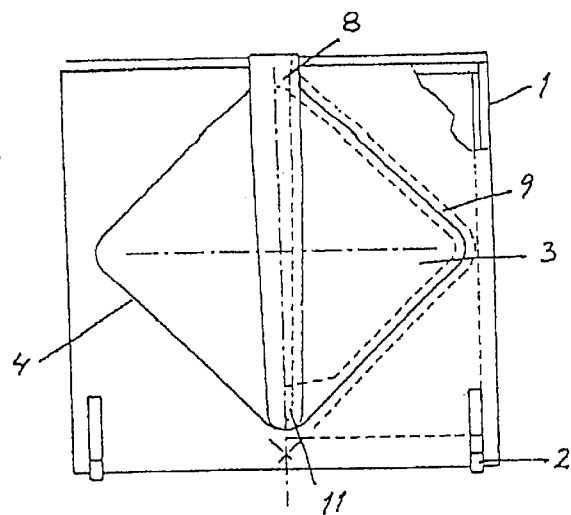
Figure 3:
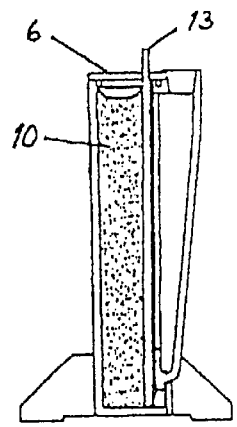
FIG. 3 shows the device according to FIG. 2 in a side view, FIGS. 4 a–c show the steps of the inventive method.

As can be seen, especially from FIG. 1b, the concentration chamber in this embodiment is a separate unit provided with a flange 9 at its circumference. With the absorbent container 1 filled with resilient absorbing material 10 the device can be assembled by sliding the chamber 3 into a snap-in position in the aperture 4 from the top of the container.

With a design like this the concentration chamber 3 and the absorbent container 1, already provided with the absorbing material in solid form, e.g. sheet form, may be kept separate during shipping and storage and then being assembled before use. The advantage of such an arrangement is that the wetting agents of the membrane will not be dried out by the absorbing material and the expected shelf-life of the device will be considerably increased.

If the absorbent material is less resilient a pressure plate of some resilient material could be inserted into the absorbent container 1 to press the absorbent material against the membrane and at the same time keep the concentration chamber in its snap-in position.

At the bottom of the concentration chamber 3 and as an integrated part of the same, below the effective membrane surface, a pocket for the retentate 11 is arranged. This pocket could be separated from the membrane surface by means of a separation wall 12, cf. FIGS. 1b and 1c. The volume of this pocket could be in the order of 15–50 microliter. The arrangement will avoid concentration to dryness. As the plastic of the wall of the chamber and consequently of the separation wall 12 is hydrophobic, there will be no capillary effect causing continued concentration when the level of the liquid has reached the level of the separation wall.

Figure 1C:
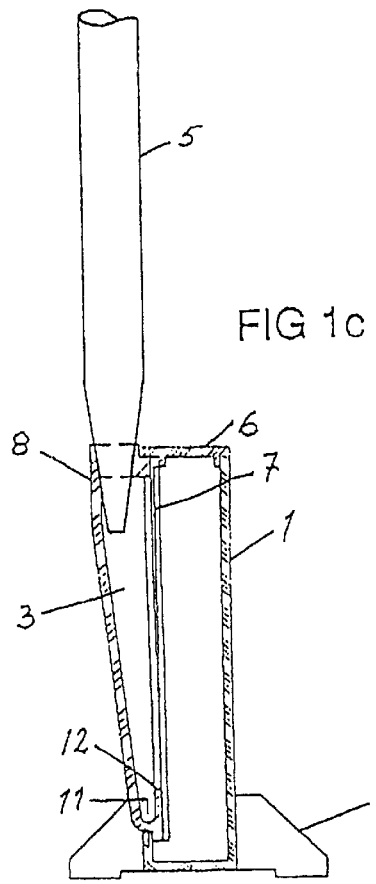

In FIG. 1c the top edge of the wall has been shown flat, perpendicular to the membrane surface. This part of the wall could, however, have another shape e.g. being formed as a ramp declining in the direction from the membrane.

In certain prior art devices a corresponding pocket is created by means of a special treatment of the membrane surface at the bottom of the concentration chamber. The retentate pocket will thus be defined between the fixed wall of the concentration chamber and the flexible membrane, the distance of which to the fixed wall could vary. The volume of the pocket thus created will obviously be difficult to define exactly.

The advantages of the arrangement according to the invention are obvious. It will be much easier to create a pocket with an exact, predetermined, volume and there will be no pre-treatment of the membrane before this is fixed to the chamber.

With a device according to the prior art as shown in U.S. Pat. 3,817,379 the concentration time will be relatively long. The combination of the fact that the concentration chamber has to contain the total volume of the liquid to be concentrated and the wish to expose this volume to a membrane area as large as possible has led to a design of the chamber which is relatively tall and thin.

This means that a very thin and long, non-volumetric pipette, e.g. a glass Pasteur-pipette has to be used for collecting the concentrate at the bottom of the chamber after the concentration has been finished. The concentrate has then to be put in a transfer tube or equivalent before it is picked up by means of a volumetric pipette for the subsequent transfer of a defined volume to an electrophoresis plate.

Figure 4A:
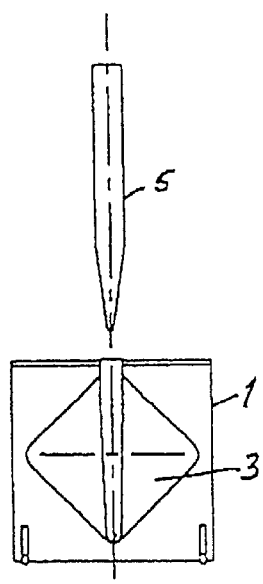
Figure 4B:
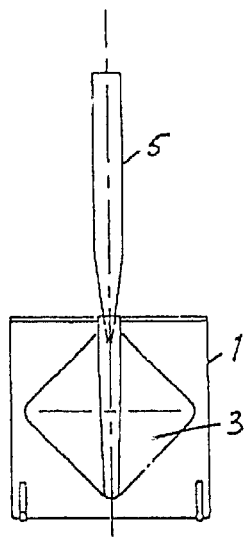
Figure 4C:
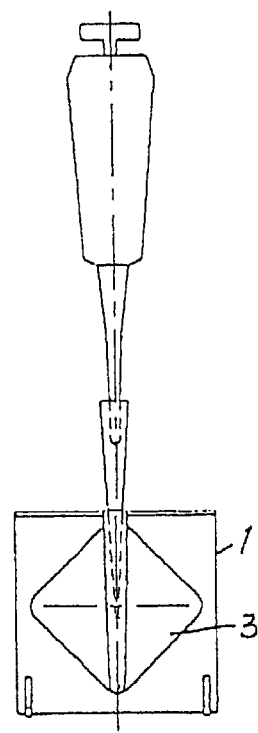

The design according to the invention allows on the other hand the use of a standard volumetric pipette. In FIG. 4c it is shown how the use of a special so called "gel pipette tip" allows the direct pick-up and transfer of a defined volume of retentate for further processing.

Figure 2:
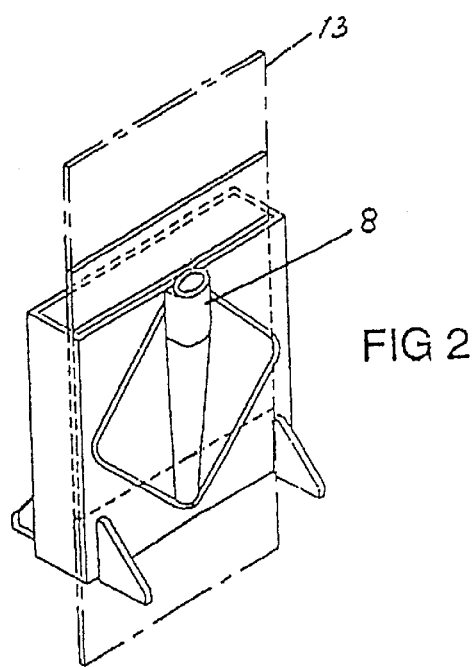
FIG. 2 shows the same device additionally provided with an adjustable separator between the absorbent material and the membrane.

FIG. 2 shows a special feature of an embodiment of the invention. On the inside of the wall of the absorbent container provided with the aperture 4, an impermeable separator 13 suitably in the form of a plate or a film is arranged so that it could be pulled upwards or downwards. Assuming the separator has the form of a slidable plate. By pulling it upwards the maximum effective membrane area could obviously be controlled between zero and full area. By pulling it downwards the dead-stop of the concentration could be controlled.

In one embodiment of the method according to the invention the separator sheet is raised to expose partially or completely the membrane to the absorbent material behind it. With the separator fully retracted, the maximum membrane surface area becomes active, resulting in faster filtration but significant protein binding due to the larger active membrane surface. A smaller membrane exposure to the absorbent will result in slower speed but will also decrease the protein binding into the inactive portions of the membrane.

Additionally, if the device is provided with this feature it could be shipped and stored assembled even with very strong absorbing agents such as silica gel or other hydrophilic particles. The lack of contact between the membrane and the absorbent material used in the device greatly reduces membrane degradation due to wetting agents absorbing onto an exposed absorbent material which allows the use of high performance absorbents.

When the separator is in the form of a film it could be bonded or sealed to the side of the absorbent container 1.

This feature makes it convenient to use powders of absorbent material such as silica gel which will fill the irregular contours of the membrane surface providing improved membrane contact and regularity of filtration.

It is understood that there does not have to be any liquid-tight sealing between the absorbent container and the separator. When the separator is in the form of a plate and being arranged to be pulled downwards it could be provided with notches so that the excessive parts could be broken off.

The device which has been described so far is a single device with one concentration chamber and one absorbent container. A multiple device could of course be envisaged with several concentration chambers side by side. Even if in a multiple device a common absorbent container should be used it is obvious that the risk for cross contamination is less than in a multiple device according to the prior art due to the design with a separate membrane for each concentration chamber and the closest point on the adjacent membrane being a corner and not a long side.

In the method according to the invention the first step comprises filling the concentration chamber preferably but not necessarily by means of a standard laboratory pipette. The pipette with a volume of e.g. 10 ml is first loaded with the liquid to process. The liquid is transported by means of the pipette to the entry port of the concentration chamber. A volume of about 2,0 ml of this liquid is filled into the lower part of the device, i.e the concentration chamber 3 having a nominal volume of 2,5 ml, while letting the air escape at the side of the pipette, cf. FIG. 4a. The flow of liquid is then stopped by blocking the upper opening of the pipette and the pipette is fixed and locked liquid-tight to the concentration chamber as an auxiliary reservoir, and then the pipette is again released. cf. FIG. 4b. A conical fit, as shown in FIG. 1c, could be appropriate but any liquid-tight fit would do.

To use a pipette as auxiliary reservoir is of course very advantageous. The high liquid column will give an advantageous hydrostatic pressure in the concentration chamber which will speed up the concentration. Additionally the provision of a special reservoir is avoided. Such a special reservoir could, however, be envisaged especially when large volumes of liquid are to be processed.

If the pipette is allowing the air to exit through the pipette during the filling of the concentration chamber the fixing of the pipette to the opening of the chamber could be carried out before the liquid is filled into the device.

When the concentration has finished the next step would be to take out the retentate from the pocket and transfer a specified volume of the same to an electrophoresis plate for analysis.

The relatively small vertical dimension of the concentration chamber in connection with the large opening makes it possible in the device according to the invention to reach the retentate pocket for a quantitative recovery of final concentrate by means of a standard conical micro volume pipette tip, thereby avoiding an intermediate vessel necessary according to the prior art.

Concentration with reduced effective membrane area could according to the above achieved by making use of the separator which would then be pulled upwards leaving only part of the membrane surface exposed to the liquid.

The same effect could bed with the device according to the invention as follows The concentration chamber is only partly filled with liquid up to a certain predetermined level. Then the pipette containing the rest of the liquid will, be fixed tightly to the chamber. If the air can not escape from the chamber and the hole in the tip of the pipette is small enough an equilibrium with only part of the membrane surface effective will be reached in which state liquid passing through the membrane will be automatically replaced with liquid from the pipette.

The device, used in a similar way, will also make it possible to wash macromolecules in a solution. The only difference in relation to the above method would be that a pipette containing a second liquid, e.g. a buffer solution, will be fixed to the concentration chamber. The liquid passing the membrane will thus be replaced with buffer solution.

The washing process could be preceded by a concentration stage. The concentration chamber could e.g. first be filled to a volume of 2,0 ml with a liquid containing macromolecules. This sample is then left to concentrate down to let say 0,2 ml. Thereafter the auxiliary reservoir containing buffer solution is fixed to the chamber and the washing is carried out according to the above.

What is claimed is:

1. In a device for removing or replacing solvent in a liquid sample containing macromolecules comprising a concentration chamber (3) having at least one rigid wall and one opposite wall formed from a membrane (7) permeable to said solvent, an aperture adjacent an upper part of said concentration chamber for introduction and removal of liquid, a pocket (11) in its lower portion for retaining a fixed volume of a concentrated sample, and an absorption container (1) provided with absorbent material (10) arranged closely adjacent said membrane wall of said concentration chamber and capable of absorbing said solvent, the improvement comprising said aperture adjacent the upper end of said concentration chamber arranged to receive an outlet of a detachable auxiliary upper reservoir (5), and means for providing gas-tight or liquid-tight seal between said auxiliary reservoir and the concentration chamber when said auxiliary reservoir is received in said aperture in the concentration chamber.

2. Device according to claim 1 wherein the concentration chamber (3) has a generally flat, rectangular form arranged to be positioned for use with one diagonal oriented in a vertical direction.

3. Device according to claim 2 wherein said concentration chamber (3) is mounted with a snap-in fit in an aperture (4) in a side wall of said absorbent container (1).

4. Device according to claim 3 wherein an impermeable separator (13) is arranged in the absorbent container (1) covering said aperture (4) and that said separator is arranged to be partly removed from said aperture (4) to expose only part of the membrane (7) of the cooperating concentration chamber (3) to said absorption material (10).

5. Device according to claim 1 wherein the aperture adjacent the upper part of the concentration chamber (3) is designed to allow quantitative recovery of final concentrate from said pocket (11) by means of a standard conical gel loader pipette tip.

6. Device according to claim 1 wherein said auxiliary reservoir (5) is constituted by a pipette.

7. Device according to claim 1 wherein said pocket (11) in the lower portion of the concentration chamber is separated from the membrane surface by means of a separation wall (12) of hydrophobic material interrupting the capillary effect tending to continue concentration when the liquid level has reached the level of the separation wall.

8. In a device for removing or replacing solvent in a liquid sample containing macromolecules comprising a concentration chamber (3) having at least one rigid wall and one opposite wall formed of a membrane (7) permeable to said solvent, an aperture adjacent an upper part of said concentration chamber for introduction and removal of liquid, a pocket (11) in its lower portion for retaining a fixed volume of a concentrated sample, and an absorption container (1) provided with absorbent material (10) arranged closely adjacent said membrane wall of said concentration chamber and capable of absorbing said solvent, the improvement comprising a detachable auxiliary upper reservoir (5) arranged fixed to said aperture adjacent the upper end of said concentration chamber, and means for providing a gas-tight or liquid-tight seal between said auxiliary reservoir and the concentration chamber (3) when said auxiliary reservoir (5) is received in said aperture in the concentration chamber (3).

9. Device according to claim 8 characterized in that the concentration chamber (3) has a generally flat, rectangular form arranged to be positioned for use with one diagonal oriented in a vertical direction.

10. Device according to claim 9 wherein said concentration chamber (3) is mounted with a snap-in fit in an aperture (4) in a side wall of the absorbent container (1).

11. Device according to claim 10 wherein an impermeable separator (13) is arranged in the absorbent container (1) covering said aperture (4) and that said separator is arranged to be partly removed from said aperture (4) to expose only part of the membrane (7) of the cooperating concentration chamber (3) to said absorption material (10).

12. Device according to claim 8 wherein the aperture adjacent the upper part of the concentration chamber (3) is designed to allow quantitative recovery of final concentrate from said pocket (11) by means of a standard conical gel loader pipette tip.

13. Device according to claim 8 wherein said auxiliary reservoir (5) is constituted by a pipette.

14. Device according to claim 8 wherein said pocket (11) in the lower portion of the concentration chamber is separated from the membrane surface by means of a separation wall (12) of hydrophobic material interrupting the capillary effect tending to continue concentration when the liquid level has reached the level of the separation wall.

15. In a method for concentrating a liquid sample containing macromolecules and a solvent by means of a device comprising a concentration chamber (3) having at least one rigid wall and one opposite wall formed of a membrane (7) permeable to said solvent, an aperture adjacent the upper part of said concentration chamber for introduction and removal of liquid, a pocket (11) in its lower portion for retaining a fixed volume of a concentrated sample, and an absorption container (1) provided with absorbent material (10) arranged closely adjacent said membrane wall of said concentration chamber and capable of absorbing said solvent, the improvement comprising the following steps:

a—the concentration chamber is filled with part of the liquid sample up to a predetermined level, b—a detachable auxiliary upper reservoir (5) containing the rest of the liquid sample is tightly fixed to the aperture adjacent the upper end of said concentration chamber to successively deliver additional liquid sample as the concentration is progressing.

16. In a method for washing macromolecules in a liquid sample containing macromolecules and a solvent by means of a device comprising a concentration chamber (3) having at least one rigid wall and one opposite wall formed of a membrane (7) permeable to said solvent, an aperture adjacent the upper part of said concentration chamber for introduction and removal of liquid, a pocket (11) in its lower portion for retaining a fixed volume of a concentrated sample, and an absorption container (1) provided with absorbent material (10) arranged closely adjacent said membrane wall of said concentration chamber and capable of absorbing said solvent, the improvement comprising the following steps:

a—the concentration chamber is filled with the liquid sample up to a predetermined level, b—a detachable auxiliary upper reservoir (5) containing a solvent or buffer solution is tightly fixed to the aperture adjacent the upper end of said concentration chamber to successively deliver solvent or buffer solution as a replacement for the liquid absorbed by the absorption material.

* * * * *